United States Patent [19]

Numata et al.

[11] 4,179,502

[45] Dec. 18, 1979

[54] 7[2-HYDROXYIMINOACETAMIDO]CEPH-ALOSPORINS

[76] Inventors: Mitsuo Numata, 25-13, Ankojicho 4-chome, Takatsuki, Osaka, Japan, (569); Isao Minamida, 526-13, Oharano-kamisatominaminocho, Nishikyo-ku, Kyoto, Japan, (615); Susumu Tsushima, A1-1201, 8 Momoyamadai 2-chome, Suita, Osaka, Japan, (565)

[21] Appl. No.: 877,746

[22] Filed: Feb. 14, 1978

[30] Foreign Application Priority Data

Feb. 17, 1977 [JP] Japan .................................. 52/16994

[51] Int. Cl.$^2$ .................. A61K 31/545; C07D 501/20
[52] U.S. Cl. ...................... 424/246; 544/22; 544/26; 544/27
[58] Field of Search .......................... 544/22, 27, 26; 424/246

[56]  References Cited
U.S. PATENT DOCUMENTS 4,033,950  7/1977  Cook et al. ............................ 544/22

FOREIGN PATENT DOCUMENTS 852860  9/1977 Belgium.
2556736  6/1976 Fed. Rep. of Germany.

*Primary Examiner*—David Wheeler
*Attorney, Agent, or Firm*—Hubbell, Cohen, Stiefel & Gross

[57]  ABSTRACT

2-Hydroxyiminoacetamide compounds of the following formula and salts thereof:

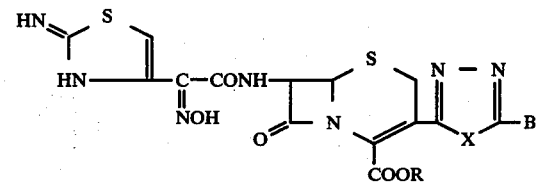

[wherein X is S, O or an imino group which may optionally be substituted; B is a hydrogen atom or a hydroxyl, amino, mercapto or hydrocarbon residue group which may optionally be substituted; and COOR is a carboxyl group which may optionally be esterified] and pharmaceutically acceptable salts thereof are novel and useful as antibacterial agents.

5 Claims, No Drawings

7[2-HYDROXYIMINOACETAMIDO]CEPHALOSPORINS

NOVEL CEPHALOSPORIN DERIVATIVES

This invention relates to novel cephalosporin antibiotics which are of value as prophylactic and therapeutic agents for the management of diseases in animals including domestic fowls and human beings and, particularly, for the treatment of infectious diseases in said animals caused by gram-positive or gram-negative bacteria. More concretely, this invention relates to 2-hydroxyiminoacetamide compounds of the general formula [I]:

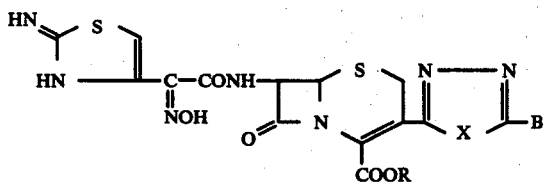

[wherein X is S, O or an imino group which may optionally be substituted; B is a hydrogen atom or a hydroxyl, amino, mercapto or hydrocarbon residue group which may optionally be substituted; and COOR is a carboxyl group which may optionally be esterified] and to pharmaceutically acceptable salts thereof.

Today several types of semi-synthetic cephalosporins known to possess broad antibacterial spectra are commercially available and have been clinically employed for the management of various infectious diseases. However, it has been reported that those agents are not practically active against all the pathogenic bacteria encountered in clinical situations. For example, it is reported that certain strains of *Escherichia coli*, certain *Citrobacter* bacteria, a large majority of indole-positive pathogenic bacteria of the genus *Proteus*, the genus *Enterobacter*, the genus *Serratia* and the genus *Pseudomonas* are cephalosporin-resistant (Warren E. Wick, Cephalosporins and Penicillins; Chemistry and Biology, Chapter 11, edited by E. H. Flynn, Academic Press, 1972). Therefore, a search for new cephalosporins clinically applicable to these pathogens is still being continued.

Under these circumstances, the present inventors have continued to create a vast number of new cephalosporin derivatives and to examine their pharmaceutical properties. Now they have succeeded in synthesizing the above cephalosporin derivatives [I] and their salts, and have found that those compounds inhibit a large variety of bacteria including Gram-positive bacteria and Gram-negative bacteria.

Particularly, the beneficial features of the antimicrobial activity of the compounds of this invention are as follows. A preferred group of compounds of this invention not only display practically sufficient activity against Gram-positive bacteria including *Staphylococcus aureus* but also exhibit activity against a broad spectrum of Gram-negative bacteria including *Escherichia coli*, *Klebsiella pneumoniae*, *Proteus vulgaris*, *Proteus mirabilis*, *Proteus morganii*, *Proteus rettgeri*, *Citrobacter freundii*, *Enterobacter cloacae* and *Serratia marcescens*.

Referring to the general formula [I], the optionally substituted imino group X may be represented by

and $Z^1$ may for example be hydrogen, a straight or branched chain lower alkyl group (preferably containing 1 to 3 carbon atoms), e.g. methyl or ethyl, or an acyl group derived from a lower carboxylic acid (preferably containing 1 to 5 carbon atoms), e.g. formyl, acetyl, propionyl or the like.

The hydroxyl, amino, mercapto or hydrogen residue group, as represented by the symbol B, may be substituted. The hydrocarbon residue may for example be a straight or branched chain lower alkyl group (preferably containing 1 to 3 carbon atoms), e.g. methyl, ethyl or isopropyl, an aryl group such as phenyl, or an aralkyl group such as benzyl. As exemplary substituents of said hydroxyl, amino, mercapto and hydrocarbon residue group, there may be mentioned a straight or branched chain lower alkyl group (preferably including 1 to 3 carbon atoms), e.g. methyl, ethyl or isopropyl, and an acyl group derived from a lower carboxylic acid (preferably containing 1 to 5 carbon atoms), e.g. formyl, acetyl or propionyl. When B is an amino group, one or two substituents may be present and, in that case, the substituents may be the same or different. As examples of such substituted amino group may be mentioned dimethylamino, N-acetyl-N-methylamino, etc.

As examples of the ester residues R and R' (below-mentioned) of the esterified carboxyl groups COOR and COOR' (below-mentioned), there may be mentioned benzyl, p-nitrobenzyl, di- or trialkylsilyl, alkoxysilyl, benzhydryl, alkoxyalkyl, trichloroethyl, methylsulfonylethyl, t-butyl, methoxybenzyl, trityl, methylthiomethyl, acetyloxymethyl, pivaloyloxymethyl, ethoxycarbonyloxymethyl, α-ethoxycarbonyloxyethyl, etc. The ester residue may be of any kind, so long as it may be easily cleaved by an expedient chemical treatment (such as hydrolysis, reduction, acid decomposition, etc.) or if after administration of the compound, said residue may detach itself readily in the patient's body. A large number of such ester residues are known other than those enumerated above in the field of cephalosporins and penicillins and any of them can be employed in the practice of this invention. Any of the residues R and R' may be hydrogen.

As regards the salt of compound of general formula [I], there may be conveniently employed any salts generally known to be pharmaceutically acceptable in the field of cephalosporins and penicillins. Thus, there may be mentioned at the carboxyl function, e.g. the salts such as salts with inorganic bases including alkali metals and alkaline earth metals such as sodium, potassium, lithium, etc., the salts with organic bases such as basic amino acids including arginine, ornithine, lysine, histidine, etc., dimethylamine, dicyclohexylamine, trimethylamine, diethanolamine, di-n-butylamine, etc.; the salts with inorganic acids such as hydrochloric acid, sulfuric acid, hydrobromic acid, nitric acid and the salts with organic acids such as maleic acid, oxalic acid, etc. at the basic function in the acyl group of of the 7-position or the imino function of the iminothiazoline part or, in certain instances, at the basic function of the substituent of the 3-position.

The compounds of the invention may assume two tautomeric forms, due to the tautomerization represented by the following formulas:

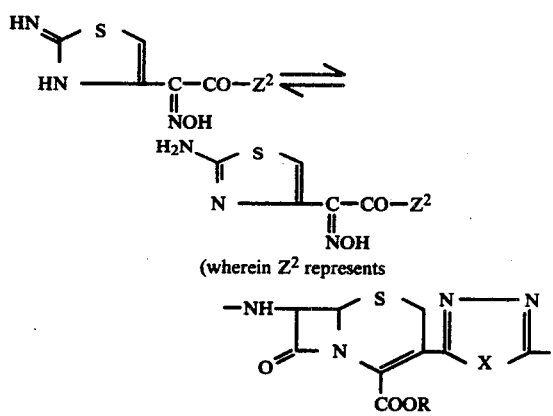

(wherein $Z^2$ represents

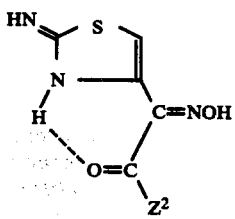

the other symbols, i.e. X, B and R are as defined above.

Many investigations have been made on the form in which compounds of this type exist, and while some literature refer to the thiazoline form (G. J. Kruger & G. Gafner, Acta Cryst. B 27, 326 (1971), and J. M. Vandenbelt & L. Doub, J. Am. Chem. Soc. 66, 1633 (1944)), other reporters refer to the thiazole form (L. M. Werbel, Chem. & Ind., 1966, 1634). However, various measurements seem to indicate that the compounds [I] of this invention invariably predominantly assume the thiazoline form, because of the stabilization of this form by the contributory influence of hydrogen bonding, as depicted in the following formula.

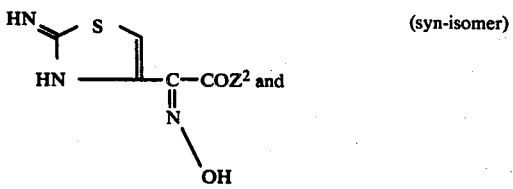

However, as is often the case with this type of equilibrium, the equilibrium is volatile and subject to change due to the circumstances in which the compounds are present, viz. due to such factors as the pH of the solvent, the polarity of the solvent, temperature and the types of substituents. Therefore, notwithstanding the appropriateness of naming the compounds of this invention either way, we designate all the compounds according to the thiazoline form throughout this specification and the claims. It is to be understood that this invention encompasses all the above tautomers.

With regard to the NOH group in the above formula, the compound of this invention includes the following two geometric isomers.

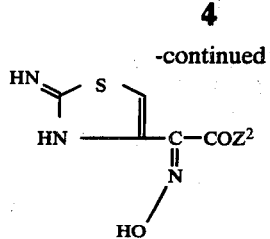
(syn-isomer)

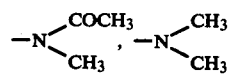
(anti-isomer)

[wherein $Z^2$ is as defined above]. Therefore, this invention encompases the syn-isomers, anti-isomers and optional mixtures of syn- and anti-isomers. However, it is interesting that the syn-isomer has stronger antibacterial activity than the corresponding anti-isomer in the compounds of the present invention.

An important class of compounds according to the present invention are those of the general formula [I], wherein X is O or S, R is hydrogen, pivaloyloxymethyl or α-ethoxycarbonyloxyethyl, and B is —NHCOCH₃, $$-N\begin{array}{c}COCH_3\\CH_3\end{array},\quad -N\begin{array}{c}CH_3\\CH_3\end{array}$$

or —CH₃, or a pharmaceutically acceptable salt thereof, the pharmaceutically acceptable salt being as defined above.

Among the preferred compounds of this invention, there may be mentioned, for example, 7-[2-(2-imino-4-thiazolin-4-yl)-2-hydroxyimino]acetamido-3-(5-amino-1,3,4-thiadiazol-2-yl)-3-cephem-4-carboxylic acid (syn-isomer); 7-[2-(2-imino-4-thiazolin-4-yl)-2-hydroxyimino]acetamido-3-(5-acetylamino-1,3,4-thiadiazol-2-yl)-3-cephem-4-carboxylic acid (syn-isomer); 7-[2-(2-imino-4-thiazolin-4-yl)-2-hydroxyimino]acetamido-3-(5-methyl-1,3,4-thiadiazol-2-yl)-3-cephem-4-carboxylic acid (syn-isomer); 7-[2-(2-imino-4-thiazolin-4-yl)-2-hydroxyimino]acetamido-3-(1,3,4-thiadiazol-2-yl)-3-cephem-4-carboxylic acid (syn-isomer); 7-[2-(2-imino-4-thiazolin-4-yl)-2-hydroxyimino]acetamido-3-(5-acetylamino-1,2,4-triazol-3-yl)-3-cephem-4-carboxylic acid (syn-isomer); 7-[2-(2-imino-4-thiazolin-4-yl)-2-hydroxyimino]-acetamido-3-(5-acetylamino-1,3,4-oxadiazol-2-yl)-3-cephem-4-carboxylic acid(syn-isomer); 7-[2-(2-imino-4-thiazolin-4-yl)-2-hydroxyimino]acetamido-3-(5-dimethylamino-1,3,4-thiadiazol-2-yl)-3-cephem-4-carboxylic acid(syn-isomer); 7-[2-(2-imino-4-thiazolin-4-yl)-2-hydroxyimino]acetamido-3-(5-(N-acetyl-N-methyl)amino-1,3,4-thiadiazol-2-yl)-3-cephem-4-carboxylic acid(syn-isomer), etc. as well as their corresponding pharmaceutically acceptable salts.

The product compounds of this invention, that is, the compounds of general formula [I] and its salts, can be produced by a method comprising reacting a compound of general formula [II]:

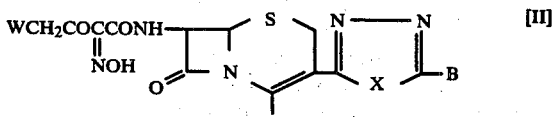

[wherein W is halogen; X is S, O or an imino group which may optionally be substituted; B is hydrogen or a hydroxyl, amino, mercapto or hydrocarbon residue group which may optionally be substituted; and COOR' is a carboxyl group which may optionally be esterified]

or a salt thereof to react with thiourea. The amount of thiourea is optional, so long as it is at least equimolar with respect to the compound [II], although the range of about 1 to 5 equivalents is appropriate in consideration of the ease of isolation and purification of the product compound. Normally this reaction is preferably conducted in a suitable organic solvent such as dimethylformamide, dimethylacetamide, dimethylsulfoxide, hexamethylphosphoramide or other polar aprotic solvents. In certain cases, the reaction may be conducted in a solvent mixture of the above-mentioned solvents with tetrahydrofuran, acetone, alcohol, water or other solvents. The reaction proceeds with sufficient readiness at room temperature, although it is normally carried out at about 0° to about 80° C. The compound can be isolated by such procedures as crystallization and precipitation as the hydrogen halide salt or, alternatively, by such per se known procedures as solvent extraction, alteration of pH, phasic transfer, crystallization, recrystallization or chromatography as the free form (inclusive of the zwitterion form) or a salt thereof. When the syn-isomer [II] is used as the starting compound, the product compound is obtained in the syn-form, whereas the use of the anti-isomer [II] usually results in the production of the anti-isomer [I]. When the 4-carboxyl group of the compound has been esterified, a deesterification reaction is carried out if desired. On the other hand, when the 4-carboxyl group of the compound is a free carboxyl group, the compound may be further subjected to esterification. The deesterification and esterification reactions can be carried out by procedures known per se.

Referring to the general formula [II], halogen represented by W may be chlorine or bromine; the examples of X and B are as defined above; and examples of the salt may be those of the salts with the bases or acids, which are mentioned above regarding the pharmaceutically acceptable salt of the compound [I]. The examples of R' may be the same as for those of R, which are defined.

The compounds of general formula [II] and salts thereof which are employed in the practice of this invention are all novel and it should be emphasized that they are useful as intermediates, not only for the production of the compounds of this invention, but also for the production of various other useful antibiotics.

This compound [II] or its salts can be produced by reacting a compound of formula [III]:

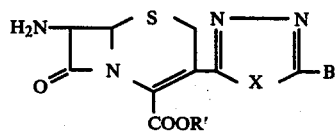

[wherein COOR', X and B are as defined above] or its salt with a compound of formula [IV];

WCH₂COCH₂COW'  [IV]

[wherein W is as defined above; and W' is halogen, e.g. chlorine or bromine] to obtain a compound of general formula [V]:

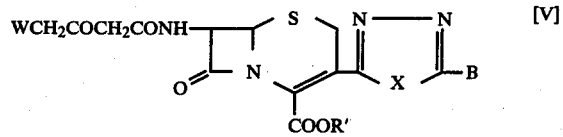

or its salts [wherein W, COOR', X and B are as defined above] and, then, subjecting the last-mentioned compound to nitrosation.

The reaction of compound [III] or any of its salts with compound [IV] may be carried out by methods known per se [e.g. Japanese Patent Application Laid-open No. 138696/1976]. Normally this reaction is carried out in a solvent (e.g. water, acetone, acetonitrile, dimethylformamide, dimethylacetamide, dichloromethane, dioxane, etc.) at about −70° C. to +40° C. and, preferably, in the presence of a base (e.g. sodium carbonate, sodium hydrogen carbonate, triethylamine, dibutylamine, dicyclohexylamine, pyridine, collidine, etc.). It is preferable to employ about 1 to 2 molar equivalents of compound [IV] or any of its salts per mole of compound [III]. The compound [V] or its salts thus produced may be isolated by such procedures as concentration, phasic transfer, chromatography, crystallization and recrystallization, or alternatively, may be subjected to nitrosation without being so isolated. The nitrosation reaction may also be carried out by a process known per se. This nitrosation reaction can be accomplished by contacting compound [V] or any of its salts to with a nitrosating agent. While the nitrosating agent may for example be nitrous acid, methyl nitrite, ethyl nitrite or amyl nitrite, the use of sodium nitrite under acidic conditions as established by acetic acid or hydrochloric acid is most desirable from an economic point of view. This reaction is carried out in a solvent. The solvent may be any solvent inert to the reaction. Thus, normally, dioxane, acetonitrile, tetrahydrofuran, acetic acid, methanol, ethanol or water or a mixture thereof may be employed. The reaction is normally carried out under cooling or at room temperature for 5 minutes to 2 hours. This nitrosation reaction yields the hydroxyimino compound [II] or its salts having the syn configuration with respect to the acylamido group (i.e. syn-isomer). In certain instances, the reaction gives rise to a small proportion of the anti-isomer of the compound [II] or its salts together with the syn-isomer [II] or its salt. However, the proportion of syn-isomer is predominant and the syn-isomer can be easily separated from the anti-isomer by recrystallization, chromatography or another conventional procedure.

The compound of this invention can be produced by other per se known procedures. For example, it can be produced by a method comprising reacting a compound of the above formula [III] or any of its salts with a compound of formula [VI]:

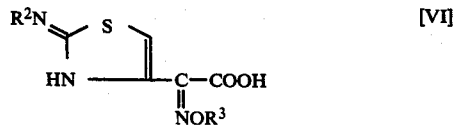

[wherein R²N is an imino group which may optionally be protected and OR³ is a hydroxyl group which may optionally be protected] or a reactive derivative thereof and, if protective groups are employed, further removing those protective groups. The types of protective groups for the imino and hydroxyl functions, the methods for protection and for removal of the protective groups, the types of said reactive derivative and the method for preparation of such derivatives are well established in the penicillin and cephalosporin art and can be adopted for the purposes of this invention.

Thus, $R^2$ may be a protecting group such as formyl, an alkyl($C_{1-4}$)carbonyl group (e.g. acetyl, propionyl, etc.), a substituted alkyl($C_{1-4}$)carbonyl group (e.g. chloroacetyl etc.), an alkoxy($C_{1-4}$)carbonyl group (e.g. t-butoxycarbonyl, etc.), an alkoxy($C_{1-4}$)alkyl($C_{1-4}$)carbonyl group (e.g. methoxyacetyl, methoxypropionyl, etc.), a substituted alkoxy($C_{1-4}$)carbonyl group (e.g. trichloroethoxycarbonyl, etc.), an aralkyl($C_{7-10}$)oxycarbonyl group (e.g. benzyloxycarbonyl, etc.), or a substituted aralkyl($C_{7-10}$)oxycarbonyl group (e.g. p-nitrobenzyloxycarbonyl, etc.).

The protecting group $R^3$ is exemplified by an acyl group such as formyl, acetyl, chloroacetyl, trifluoroacetyl, methoxyacetyl, phenoxyacetyl, benzoyl, p-nitrobenzoyl, ethoxycarbonyl, $\beta,\beta,\beta$-trichloroethoxycarbonyl, $\beta,\beta,\beta$-tribromoethoxycarbonyl, p-nitrophenoxycarbonyl, and a substituted alkyl such as tetrahydrothiofuranyl, methoxy, methoxytetrahydropyranyl etc., tetrahydropyranyl and 2-methoxyethoxymethyl, and also a silyl group such as trimethylsilyl, dimethyl-t-butylsilyl, etc.

In this process, the compound [VI] is employed, either as a free compound [VI], in the form of its salt or in the form of a reactive derivative, as an acylating agent for the acylation of the amino group in the 7-position of compound [III] or a salt thereof. Thus, the free acid [VI], an alkali or alkaline earth metal salt of the free acid [VI] (e.g. sodium, potassium or calcium salt), an organic amine salt of the free acid [VI] (e.g. trimethylamine or pyridine salt), or a reactive derivative thereof [such as a corresponding acid halide (e.g. acid chloride or acid bromide), acid anhydride, mixed acid anhydride, active amide, active ester or the like] is subjected to the aforementioned reaction. As examples of said active ester there may be mentioned p-nitrophenyl ester, 2,4-dinitrophenyl ester, pentachlorophenyl ester, N-hydroxysuccinimide ester and N-hydroxyphthalimide ester. As examples of said mixed acid anhydride there may be mentioned mixed acid anhydride with a carbonic acid monoester (e.g. carbonic acid monomethyl ester or carbonic acid monoisobutyl ester) and a mixed acid anhydride with a lower alkanoic acid having one to five carbon atoms which may be substituted by halogen (e.g. pivalic acid or trichloroacetic acid). When the carboxylic acid [VI] is employed as the free acid or in the form of a salt, there is employed a suitable condensing agent. As examples of said condensing agent there may be mentioned N,N'-di-substituted carbodiimides, e.g. N,N'-dicyclohexyl-carbodiimide; azolides, e.g. N,N'-carbonylimidazole and N,N'-thionyldiimidazole; dehydrating agents, e.g. N-ethoxycarbonyl-2-ethoxy-1,2-dihydroquinoline, phosphorus oxychloride and alkoxyacetylene; 2-halopyridinium salts (e.g. 2-chloropyridiniummethyl iodide, 2-fluoropyridiniummethyl iodide) and the like. When such a condensing agent is employed, it is supposed that the reaction proceeds via the reactive derivative of the carboxylic acid [VI] coupled with the condensing agent.

This reaction between the compound [III] or a salt thereof with the acylating agent proceeds readily under per se known conditions. For example, the reaction may be conducted under conditions analogous to those disclosed in German Patent Application Laid-Open to the Public (OLS) No. P 2461478. The reaction is usually conducted in a suitable inert solvent. As examples of such solvent there may be mentioned halogenated hydrocarbons, e.g. chloroform, methylene chloride, etc.; ethers, e.g. tetrahydrofuran, dioxane, etc.; dimethylformamide; dimethylacetamide; acetone; water and mixtures thereof. The proportion of said acylating agent [VI] or a reactive derivative thereof is normally within the range of about 1 to 5, preferably 1 to 2, molar equivalents, based on the compound [III] or a salt thereof. This reaction is generally carried out at a temperature in the range of $-50°$ to $+40°$ C. The reaction time is selected from the range of one to ten hours, preferably one to three hours. Following the acylation reaction, the protective groups $R^2$ or/and $R^3$ may be removed, if desired. The removal of the protective groups $R^2$ or/and $R^3$ may be generally accomplished by procedures known per se [e.g. by the procedure described in Japanese Patent Application Laid Open No. 52083/1975 and Pure and Applied Chemistry, 7, 335(1963)] or a procedure analogous thereto.

Thus, for example, t-butoxycarbonyl represented by $R^2$ may be removed by treatment with an aqueous solution of an acid (e.g. hydrogen chloride, sulfuric acid etc.), and monochloroacetyl represented by $R^2$ may be removed by treatment with thiourea. Formyl or trifluoroacetyl represented by $R^3$ may be removed by treatment with potassium hydrogen carbonate in an aqueous methanol, and tetrahydropyranyl represented by $R^3$ may be removed by treatment with dilute hydrochloric acid. The removal of the protecting group is carried out under conditions known per se.

Whichever of the two alternative methods is adopted for the production of the compound [I] or its pharmaceutically acceptable salts, the following modifications of the end product may be carried out.

When the end product [I] is produced in the form of free acid, it can be converted into a pharmaceutically acceptable salt thereof by a per se conventional procedure.

When the end product of the present invention is obtained in the form of a salt, it can be converted into the free form or any other salt.

When the end product of the present invention is obtained in the form of free carboxylic acid or its salt at the 4 position, it may be esterified into an ester in accordance with conventional means, the kind of the ester having been described in detail above. More concretely, the ester is produced, for example, by a method, which comprises reacting a compound [I] wherein R is hydrogen or a salt thereof with a compound of the formula: Hal-R''', wherein R''' is the ester residue, the example of which may be the same as the example as above mentioned regarding the residue R.

When the end product [I] is obtained in the form of an ester, the product may be subjected to deesterification to obtain the product [I] in the form of a free carboxylic acid or a pharmaceutically acceptable salt thereof.

These modifications may be carried out by procedures known per se.

Each of the starting compounds [III], [IV] and [VI] is easily prepared by a known method or a method analogous thereto.

The compounds [I] and salts thereof according to this invention are broad-spectrum cephalosporins, that is, cephalosporins which are not only active against gram-positive bacteria but also have excellent activity against a broad range of clinically significant gram-negative microorganisms. The compounds of this invention are of low toxicity and are superior cephalosporins in that they have activity against the various gram-negative pathogenic bacteria.

The cephalosporin derivatives according to this invention can be used, for example as disinfectants and in the therapy of infections, and just as the conventional cephalosporin drugs, can be safely administered in bulk form or, incorporated with physiologically acceptable vehicles or excipients in a known manner, in the form of solution or suspension. As afore-mentioned, the syn-form of the compound of this invention is more antibacterially potent than the corresponding anti-isomer. Specifically, these compounds can be used as safe curative drugs in the therapy of diseases caused by the above-mentioned bacteria, purulent or suppurative diseases, respiratory infections, bile duct infections, intestinal infections, urinary tract infections and gyneco-obstetrical infections, and the compounds according to the present invention, preferably the compounds aforementioned as the preferred class are administered intramuscularly or intravenously at a dose level of about 1 to 20 mg daily per kg body weight in the case of an adult human, divided into 3 to 4 doses a day.

REFERENCE EXAMPLE

In 10.5 ml of dichloromethane there were dissolved 2.1 g of diketene and, under stirring, a solution of 4.00 g of bromine in 12.5 ml of dichloromethane was added dropwise at a temperature not exceeding $-20°$ C. After the dropwise addition was completed, the mixture was maintained at $0°$ C. for 10 minutes. Separately, 0.5 g of benzhydryl 7-amino-3-(5-acetylamino-1,3,4-thiadiazol-2-yl)-3-cephem-4-carboxylate was suspended in 15 ml of dichloromethane and, under stirring, 1.37 ml of the above acid bromide solution were added at a temperature not exceeding $-40°$ C. Following this dropwise addition, the mixture was stirred at room temperature for one hour. Then, a solution of 0.085 g of pyridine in 2 ml of dichloromethane was added and the mixture was further stirred for 30 minutes. A saturated aqueous solution of sodium chloride was added to the reaction mixture, which was then extracted with ethyl acetate. The ethyl acetate layer was washed with a saturated aqueous solution of sodium chloride and dried over magnesium sulfate. The solvent was evaporated off under reduced pressure and the residue was loosened up with the addition of ether. The resultant powder was recovered by filtration and dried. By the above procedure 0.383 g of benzhydryl 7-(4-bromo-3-oxobutyrylamino)-3-(5-acetylamino-1,3,4-thiadiazol-2-yl)-3-cephem-4-carboxylate was obtained.

IR $\nu_{max}^{KBr}$ cm$^{-1}$: 1789 ($\beta$-lactam), 1730 (carboxylate)

NMR(DMSO-d$_6$, ppm): 2.17(s, COCH$_3$), 3.62(s, COCH$_2$CO), 3.70, 4.02(ABq, J=18 Hz, C$_2$-H), 4.37(s, BrCH$_2$), 5.10(d, J=5 Hz, C$_6$-H), 5.68(dd, J=5 Hz & 8 Hz, C$_7$-H), 9.04(d, J=8 Hz, CONH), 12.1(broad s, —N$\underline{\text{H}}$ COCH$_3$)

EXAMPLE 1

In 4 ml of acetic acid there was dissolved 0.37 g of benzhydryl 7-(4-bromo-3-oxobutyrylamino)-3-(5-acetylamino-1,3,4-thiadiazol-2-yl)-3-cephem-4-carboxylate and, under ice-cooling and stirring, a solution of 0.048 g of sodium nitrite in 0.4 ml of water was added dropwise. After this dropwise addition, the mixture was stirred at room temperature for one hour. Then, 20 ml of a saturated aqueous solution of sodium chloride were added and extraction was carried out with ethyl acetate. The ethyl acetate layer was washed with a saturated aqueous solution of sodium chloride and dried over magnesium sulfate. The solvent was evaporated off under reduced pressure and the residue was loosened up with a solvent mixture of petroleum ether and ether (2:1 volume/volume). The resultant powder was recovered by filtration and dried. By the above procedure there was obtained 0.345 g of benzhydryl 7-(4-bromo-3-oxo-2-hydroxyiminobutyrylamino)-3-(5-acetylamino-1,3,4-thiadiazol-2-yl)-3-cephem-4-carboxylate-(syn-isomer).

IR $\nu_{max}^{KBr}$ cm$^{-1}$: 1790($\beta$-lactam)

NMR(DMSO-D$_6$, ppm): 2.18(s, CH$_3$), 3.86, 4.09(ABq, J=18 Hz, C$_2$-H), 4.60(s, BrCH$_2$-), 5.34(d, J=5 Hz, C$_6$-H), 5.99(dd, J=5 Hz & 8 Hz, C$_7$-H), 6.80(s, CH$\phi_2$), 7.0 to 7.4(m, C$_6$H$_5$), 9.46(d, J=8 Hz, CONH), 12.43(broad s, N$\underline{\text{H}}$COCH$_3$), 13.07(s, N-OH)

EXAMPLE 2

In 1 ml of dimethylacetamide there was dissolved 0.309 g of benzhydryl 7-(4-bromo-3-oxo-2-hydroxyiminobutyrylamino)-3-(5-acetylamino-1,3,4-thiadiazol-2-yl)-3-cephem-4-carboxylate-(syn-isomer) and, under stirring at room temperature, 0.036 g of thiourea was added. The mixture was stirred under the same conditions for one hour, after which ether was added and the solid product was loosened up. The resultant powder was recovered by filtration and dried. By the above procedure there was obtained 0.329 g of benzhydryl 7-[2-(2-imino-4-thiazolin-4-yl)-2-hydroxyimino]acetamido-3-(5-acetylamino-1,3,4-thiadiazol-2-yl)-3-cephem-4-carboxylate hydrobromide(syn-isomer).

IR $\nu_{max}^{KBr}$ cm$^{-1}$: 1789 ($\beta$-lactam)

NMR(DMSO-d$_6$, ppm): 2.19(s, CH$_3$), 4.00(broad s, C$_2$-H), 5.38(d, J=5 Hz, C$_6$-H), 6.00(dd, J=5 Hz & 8 Hz, C$_7$-H), 6.81(s, CH$\phi_2$), 6.91(s, thiazoline 5-H), 7.0 to 7.4(m, C$_6$H$_5$), 9.79(d, J=8 Hz, CONH), 12.42(broad, N$\underline{\text{H}}$COCH$_3$ & NOH)

EXAMPLE 3

In 1.5 ml of anisole there was suspended 0.295 g of benzhydryl 7-[2-(2-imino-4-thiazolin-4-yl)-2-hydroxyimino]acetamido-3-(5-acetylamino-1,3,4-thiadiazol-2-yl)-3-cephem-4-carboxylate hydrobromide(syn-isomer) and, under cooling with ice-water and stirring, 5 ml of trifluoroacetic acid were added. The mixture was stirred at room temperature for 20 minutes, at the end of which time the solvent was evaporated off under reduced pressure. The syrupy residue was loosened up with ether and the resultant powder was recovered by filtration and dried. By the above procedure the was obtained 0.206 g of 7-[2-(2-imino-4-thiazolin-4-yl)-2-hydroxyimino]acetamido-3-(5-acetylamino-1,3,4-thiadiazol-2-yl)-3-cephem-4-carboxylic acid hydrobromide(syn-isomer).

IR $\nu_{max}^{KBr}$ cm$^{-1}$: 1780 ($\beta$-lactam)

NMR(DMSO-d$_6$, ppm): 2.20(s, CH$_3$), 3.89, 4.16(ABq, J=18 Hz, C$_2$-H), 5.34(d, J=5 Hz, C$_6$-H), 5.92(dd, J=5 Hz & 8 Hz, C$_7$-H), 6.86(s, thiazoline 5-H), 9.70(d, J=8 Hz, CONH), 12.5(broad, N$\underline{\text{H}}$COCH$_3$ & NOH)

EXAMPLE 4

In 2 ml of water there was suspended 0.173 g of 7-[2-(2-imino-4-thiazolin-4-yl)-2-hydroxyimino] acetamido-3-(5-acetylamino-1,3,4-thiadiazol-2-yl)-3-cephem-4-carboxylic acid hydrobromide(syn-isomer) and the latter was dissolved by the addition of 0.049 g of sodium hydrogen carbonate in small installments under stirring. The solution was run onto a column of Sephadex LH-20 and development was carried out with water. The active fractions were collected and lyophilized. By the above procedure there was obtained 0.083 g of sodium 7-[2-(2-imino-4-thiazolin-4-yl)-2-hydroxyimino]-acetamido-3-(5-acetylamino-1,3,4-thiadiazol-2-yl)-3-cephem-4-carboxylate(syn-isomer).

IR $\nu_{max}^{KBr}$ cm$^{-1}$: 1766 ($\beta$-lactam)

NMR(DMSO-d$_6$, ppm): 2.17(s, CH$_3$), 3.75, 4.13(ABq, J=17 Hz, C$_2$-H), 5.19(d, J=5 Hz, C$_6$-H), 5.71(dd, J=5 Hz & 8 Hz, C$_7$-H), 6.67(s, thiazoline 5-H), 7.08(broad s, NH), 9.44(d, J=8 Hz, CONH), 11.8(broad, N$\underline{H}$COCH$_3$ & NOH)

Elemental analysis: Calcd. for C$_{16}$H$_{13}$N$_8$O$_6$S$_3$Na.3.5-H$_2$O: C, 32.27; H, 3.38; N, 18.82; Found: C, 32.26; H, 3.42; N, 18.27.

| Strain | Antimicrobial Spectrum (mcg/ml, agar dilution) | |
|---|---|---|
| | compound of this example | Cefazolin |
| S. aureus 209P | 0.78 | ≦0.2 |
| E. coli NIHJ | 0.10 | 1.56 |
| E. coli 0-111 | ≦0.012 | 0.78 |
| E. coli T-7 | 0.78 | 25 |
| K. pneumoniae DT | 0.024 | 1.56 |
| K. pneumoniae GN 3835 | 0.10 | 1.56 |
| P. vulgaris IFO 3988 | ≦0.012 | 3.13 |
| P. mirabilis GN 4359 | 0.024 | 3.13 |
| P. morganii IFO 3168 | ≦0.012 | 25 |
| P. rettgeri 8 (TNO 336) | ≦0.012 | ≦0.2 |
| P. rettgeri GN 4733 | 0.024 | 25 |
| Cit. freundii GN 99 | 0.05 | 12.5 |
| Cit. freundii GN 1706 | 0.10 | >100 |

EXAMPLE 5

By the same procedure as described in Example 1, 0.38 g of benzhydryl 7-(4-bromo-3-oxybutyrylamino)-3-(5-N-acetyl-N-methylamino-1,3,4-thiadiazol-2-yl)-3-cephem-4-carboxylate was treated with 0.048 g of sodium nitrite to obtain 0.351 g of powdery benzhydryl 7-(4-bromo-3-oxo-2-hydroxyiminobutyrylamino)-3-(5-N-acetyl-N-methylamino-1,3,4-thiadiazol-2-yl)-3-cephem-4-carboxylate(syn-isomer).

IR $\nu_{max}^{KBr}$ cm$^{-1}$: 1789 ($\beta$-lactam)

NMR(DMSO-d$_6$, ppm): 2.39(s, COCH$_3$), 3.55(s, NCH$_3$), 3.87, 4.08(ABq, J=18 Hz, C$_2$-H), 4.59(s, BrCH$_2$), 5.33(d, J=5 Hz, C$_6$-H), 5.98(dd, J=5 Hz & 8 Hz, C$_7$-H), 6.78(s, CH$\phi_2$), 7.0 to 7.4(m, C$_6$H$_5$), 9.45(d, J=8 Hz, CONH)

EXAMPLE 6

By a procedure similar to that described in Example 2, 0.31 g of benzhydryl 7-(4-bromo-3-oxo-2-hydroxyiminobutyrylamino)3-(5-N-acetyl-N-methylamino-1,3,4-thiadiazol-2-yl)-3-cephem-4-carboxylate(syn-isomer) was treated with 0.035 g of thiourea to obtain 0.310 g powdery benzhydryl 7-[2-(2-imino-4-thiazolin-4-yl)-2-hydroxyimino]acetamido-3-(5N-acetyl-N-methylamino-1,3,4-thiadiazol-2-yl)-3-cephem-4-carboxylate hydrobromide(syn-isomer).

IR $\nu_{max}^{KBr}$ cm$^{-1}$: 1789 ($\beta$-lactam)

NMR(DMSO-d$_6$, ppm): 2.40(s, COCH$_3$), 3.56(s, NCH$_3$), 4.00 (broad s, C$_2$-H), 5.40(d, J=8 Hz, C$_6$-H), 6.2(dd, J=5 Hz & 8 Hz, C$_7$-H), 6.82(s, CH$\phi_2$), 6.92(s, thiazoline 5-H), 9.80 (d, J=8 Hz, CONH)

EXAMPLE 7

By the same procedure as described in Example 3, 0.255 g of benzhydryl 7-[2-(2-imino-4-thiazolin-4-yl)-2-hydroxyimino]acetamido-3-(5-N-acetyl-N-methylamino-1,3,4-thiadiazol-2-yl)-3-cephem-4-carboxylate hydrobromide(syn-isomer) was treated to obtain 0.146 g of 7-[2-(2-imino-4-thiazolin-4-yl)-2-hydroxyimino]acetamido-3-(5-N-acetyl-N-methylamino-1,3,4-thiadiazol-2-yl)-3-cephem-4-carboxylic acid hydrobromide(syn-isomer).

IR $\nu_{max}^{KBr}$ cm$^{-1}$: 1780 ($\beta$-lactam)

NMR(DMSO-d$_6$, ppm): 2.41(s, COCH$_3$), 3.56(s, NCH$_3$), 3.90, 4.17(ABq, J=18 Hz, C$_2$-H), 5.35(d, J=5 Hz, C$_6$-H), 5.93(dd, J=5 Hz & 8 Hz, C$_7$-H), 6.87(s, thiazoline 5-H), 9.71(d, J=8 Hz, CONH)

EXAMPLE 8

0.095 g of 7-[2-(2-imino-4-thiazolin-4-yl)-2-hydroxyimino]-acetamido-3-(5-N-acetyl-N-methylamino-1,3,4-thiadiazol-2-yl)-3-cephem-4-carboxylic acid hydrobromide(syn-isomer) was dissolved by the addition of water and sodium hydrogen carbonate and the solution was treated as described in Example 4. By this procedure there was obtained 0.056 g of sodium 7-[2-(2-imino-4-thiazolin-4-yl)-2-hydroxyimino]acetamido-3-(5-N-acetyl-N-methylamino-1,3,4-thiadiazol-2-yl)-3-cephem-4-carboxylate(syn-isomer).

IR $\nu_{max}^{KBr}$ cm$^{-1}$: 1767($\beta$-lactam)

NMR(DMSO-d$_6$, ppm): 2.38(s, COCH$_3$), 3.50(s, NCH$_3$), 3.76, 4.14(ABq, J=18 Hz, C$_2$-H), 5.20(d, J=5 Hz, C$_6$-H), 5.75(dd, J=5 Hz & 8 Hz, C$_7$-H), 6.67(s, thiazoline 5-H), 7.07 (broad s, =NH), 9.42(d, J=8 Hz, CONH)

Elemental analysis: Calcd. for C$_{17}$H$_{15}$N$_8$O$_6$S$_3$Na.2-H$_2$O: C, 35.05; H, 3.29; N, 19.24: Found: C, 35.22; H, 3.51; N, 19.01.

EXAMPLE 9

By the same procedure as described in Example 1, 0.23 g of 7-(4-bromo-3-oxobutyrylamino)-3-(5-methyl-1,3,4-thiadiazol-2-yl)-3-cephem-4-carboxylic acid was treated with 0.042 g of sodium nitrite to obtain 0.198 g of 7-(4-bromo-3-oxo-2-hydroxyiminobutyrylamino)-3-(5-methyl-1,3,4-thiadiazol-2-yl)-3-cephem-4-carboxylic acid (syn-isomer) in the form of a powder.

IR $\nu_{max}^{KBr}$ cm$^{-1}$: 1786 ($\beta$-lactam)

NMR(DMSO-d$_6$, ppm): 2.56(s, CH$_3$), 3.80, 4.04(ABq, J=18 Hz, C$_2$-H), 4.60(s, BrCH$_2$), 5.34(d, J=5 Hz, C$_6$-H), 5.95(dd, J=5 Hz & 8 Hz, C$_7$-H), 9.46(d, J=8 Hz, CONH)

EXAMPLE 10

By the same procedure as described in Example 2, 0.151 g of 7-(4-bromo-3-oxo-2-hydroxyiminobutyrylamino)-3-(5-methyl-1,3,4-thiadiazol-2-yl)-3-cephem-4-carboxylic acid (syn-isomer) was treated with 0.024 g of thiourea to obtain 0.140 g of 7-[2-(2-amino-4-thiazolin-4-yl)-2-hydroxyimino]-acetamido-3-(5-methyl-1,3,4-thiadiazol-2-yl)-3-cephem-4-carboxylic acid hydrobromide(syn-isomer).

IR $\nu_{max}^{KBr}$ cm$^{-1}$: 1782 ($\beta$-lactam)

NMR(DMSO-d$_6$, ppm): 2.61(s, CH$_3$), 3.88, 4.15(ABq, J=18 Hz, C$_2$-H), 5.33(d,J=5 Hz, C$_6$-H), 5.92(dd, J=5 Hz & 8 Hz, C$_7$-H), 6.90(s, thiazoline 5-H), 9.72(d, J=8 Hz, CONH).

EXAMPLE 11

0.095 g of 7-[2-(2-imino-4-thiazolin-4-yl)-2-hydroxyimino]-acetamido-3-(5-methyl-1,3,4-thiadiazol-2-yl)-3-cephem-4-carboxylic acid hydrobromide(syn-isomer) was dissolved in water with the addition of sodium hydrogen carbonate and the solution was treated as in Example 4. By this procedure there was obtained 0.048 g of sodium 7-[2-(2-imino-4-thiazolin-4-yl)-2-hydroxyimino]acetamido-3-(5-methyl-1,3,4-thiadiazol-2-yl)-3-cephem-4-carboxylate(syn-isomer).

IR $\nu_{max}^{KBr}$ cm$^{-1}$: 1765 ($\beta$-lactam)

NMR(DMSO-d$_6$, ppm): 2.70(s, CH$_3$), 3.81, 4.16(ABq, J=18 Hz, C$_2$-H), 5.20(d, J=5 Hz, C$_6$-H), 5.78(dd, J=5 Hz & 8 Hz, C$_7$-H), 6.66(s, thiazoline 5-H), 9.41(d, J=8 Hz, CONH).

Elemental analysis: Calcd. for C$_{15}$H$_{15}$N$_7$O$_7$S$_3$Na.2-H$_2$O: C, 34.28; H, 3.07; N, 18.66: Found: C, 34.01; H, 3.31; N, 18.31.

EXAMPLE 12

By the same procedure as described in Example 1, 0.378 g of benzhydryl 7-(4-bromo-3-oxobutyrylamino)-3-(5-dimethylamino-1,3,4-thiadiazol-2-yl)-3-cephem-4-carboxylate was treated with 0.048 g of sodium nitrite to obtain 0.350 g powdery benzhydryl 7-(4-bromo-3-oxo-2-hydroxyiminobutyrylamino)-3-(5-dimethylamino-1,3,4-thiadiazol-2-yl)-3-cephem-4-carboxylate (syn-isomer).

IR $\nu_{max}^{KBr}$ cm$^{-1}$: 1788 ($\beta$-lactam)

NMR(DMSO-d$_6$, ppm): 2.90(s, CH$_3$), 3.78, 4.05(ABq, J=18 Hz, C$_2$-H), 4.61(s, BrCH$_2$), 5.33(d, J=5 Hz, C$_6$-H), 5.99(dd, J=5 Hz & 8 Hz, C$_7$-H), 6.84(s, C$\underline{H}\phi_2$), 7.0 to 7.4(m, C$_6$H$_5$), 9.47(d, J=8 Hz, CONH)

EXAMPLE 13

By the same procedure as described in Example 2, 0.300 g of benzhydryl 7-(4-bromo-3-oxo-2-hydroxyiminobutyrylamino)-3-(5-dimethylamino-1,3,4-thiadiazol-2-yl)-3-cephem-4-carboxylate (syn-isomer) was treated with 0.034 g of thiourea to obtain 0.298 g powdery benzhydryl 7-[2-(2-imino-4-thiazolin-4-yl)-2-hydroxyimino]acetamido-3-(5-dimethylamino-1,3,4-thiadiazol-2-yl)-3-cephem-4-carboxylate hydrobromide (syn-isomer).

IR $\nu_{max}^{KBr}$ cm$^{-1}$: 1790 ($\beta$-lactam)

NMR(DMSO-d$_6$, ppm): 2.97(s, CH$_3$), 4.01(broad s, C$_2$-H), 5.38(d, J=5 Hz, C$_6$-H), 6.00(dd, J=5 Hz & 8 Hz, C$_7$-H), 6.82 (s, C$\underline{H}\phi_2$), 6.90(s, thiazoline 5-H), 7.0 to 7.4(m, C$_6$H$_5$), 9.80(d, J=8 Hz, CONH).

EXAMPLE 14

By the same procedure as described in Example 3, 0.250 g of powdered benzhydryl 7-[2-(2-imino-4-thiazolin-4-yl)-2-hydroxyimino]acetamido-3-(5-dimethylamino-1,3,4-thiadiazol-2-yl)-3-cephem-4-carboxylate hydrobromide(syn-isomer) was treated to obtain 0.163 g of 7-[2-(2-imino-4-thiazolin-4-yl)-2-hydroxyimino]acetamido-3-(5-dimethylamino-1,3,4-thiadiazol-2-yl)-3-cephem-4-carboxylic acid hydrobromide (syn-isomer).

IR $\nu_{max}^{KBr}$ cm$^{-1}$: 1781 ($\beta$-lactam)

NMR(DMSO-d$_6$, ppm): 3.07(s, CH$_3$), 3.86, 4.10(ABq, J=18 Hz, C$_2$-H), 5.36(d, J=5 Hz, C$_6$-H), 5.92(dd, J=5 Hz & 8 Hz), 6.91(s, thiazoline 5-H), 9.70(d, J=8 Hz, CONH)

EXAMPLE 15

0.119 g of 7-[2-(2-imino-4-thiazolin-4-yl)-2-hydroxyimino]acetamido-3-(5-dimethylamino-1,3,4-thiadiazol-2-yl)-3-cephem-4-carboxylic acid hydrobromide(syn-isomer) was dissolved by the addition of water and sodium hydrogen carbonate and the solution was treated as in Example 4. By this procedure there was obtained 0.078 g of sodium 7-[2-(2-imino-4-thiazolin-4-yl)-2-hydroxyimino]acetamido-3-(5-dimethylamino-1,3,4-thiadiazol-2-yl)-3-cephem-4-carboxylate (syn-isomer).

IR $\nu_{max}^{KBr}$ cm$^{-1}$: 1765 ($\beta$-lactam)

NMR(DMSO-d$_6$, ppm): 3.12(s, CH$_3$), 3.78, 4.05(ABq, J=18 Hz, C$_2$-H), 5.18(d, J=5 Hz, C$_6$-H), 5.70(dd, J=5 Hz & 8 Hz, C$_7$-H), 6.67(s, thiazoline 5-H), 7.06(broad s, =NH), 9.43(d, J=8 Hz, CONH).

Elemental analysis: Calcd. for C$_{16}$H$_{15}$N$_8$O$_5$S$_3$Na.2.5-H$_2$O: C, 34.10; H, 3.58; N, 19.88: Found: C, 33.91; H, 3.83; N, 19.60.

What is claimed is:

1. A 2-hydroxyiminoacetamide of the formula:

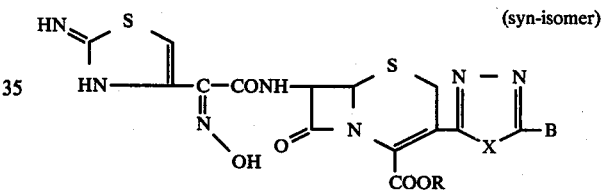

(syn-isomer)

wherein X is S; B is —NHCOCH$_3$, and R is hydrogen and pharmaceutically acceptable salts thereof.

2. A compound as claimed in claim 1, which is 7-[2-(2-imino-4-thiazolin-4-yl)-2-hydroxyimino]acetamido-3-(5-acetylamino-1,3,4-thiadiazol-2-yl)-3-cephem-4-carboxylic acid hydrobromide (syn-isomer).

3. A compound as claimed in claim 1, which is sodium 7-[2-(2-imino-4-thiazolin-4-yl)-2-hydroxyimino]acetamido-3-(5-acetylamino-1,3,4-thiadiazol-2-yl)-3-cephem-4-carboxylate (syn-isomer).

4. A method for the treatment of diseases caused by bacteria, which comprises internally administering to a human a pharmaceutically effective amount of the compound as claimed in claim 1.

5. An antibacterial composition, which comprises a therapeutically effective amount of the compound as claimed in claim 1 and a pharmaceutically acceptable carrier thereof.

* * * * *

UNITED STATES PATENT OFFICE
CERTIFICATE OF CORRECTION

Patent No. 4,179,502          Dated 12/18/79

Inventor(s) MITSUO NUMATA et al

It is certified that error appears in the above-identified patent and that said Letters Patent are hereby corrected as shown below:

Column 2, line 12: "hydrogen" should read --hydrocarbon--.

Column 3, line 57: "NOH" should read --$\overset{\|}{N}OH$--.

Column 6, line 33: "to with" should read --with--.

Column 10, line 54: "the was" should read --there was --.

Signed and Sealed this

Twenty-fourth Day of February 1981

[SEAL]

Attest:

RENE D. TEGTMEYER

Attesting Officer       Acting Commissioner of Patents and Trademarks